United States Patent [19]

Griffith

[11] Patent Number: 4,647,674
[45] Date of Patent: Mar. 3, 1987

[54] BIS-(DIBENZO[B,D]PYRANYLOXY) PROPANES

[75] Inventor: Ronald C. Griffith, Pittsford, N.Y.

[73] Assignee: Pennwalt Corporation, Philadelphia, Pa.

[21] Appl. No.: 784,979

[22] Filed: Oct. 7, 1985

[51] Int. Cl.[4] .......................................... C07D 407/00
[52] U.S. Cl. .................................... 549/280; 514/455
[58] Field of Search ........................................ 549/280

[56] References Cited

U.S. PATENT DOCUMENTS

| | | | |
|---|---|---|---|
| 3,649,650 | 3/1972 | Razdan et al. | 549/390 |
| 4,066,667 | 1/1978 | Lee et al. | 549/280 |
| 4,118,559 | 10/1978 | Johnson et al. | 546/256 |
| 4,126,694 | 11/1978 | Razdan et al. | 514/454 |
| 4,126,695 | 11/1978 | Razdan et al. | 514/454 |
| 4,206,225 | 6/1980 | Johnson | 514/228 |
| 4,569,994 | 2/1986 | Griffith | 544/150 |

OTHER PUBLICATIONS

Gesquiere J. C. et al. Ann. Pharmaceutiquies Francasises 40 (3), 251-257 (1982).

Primary Examiner—Jane T. Fan

[57] ABSTRACT

Dibenzopyrone derivatives which possess depressant and/or antihypoxia activity are 1,3-bis(dibenzo[b,d-]pyranyloxy propanes having the formula (1):

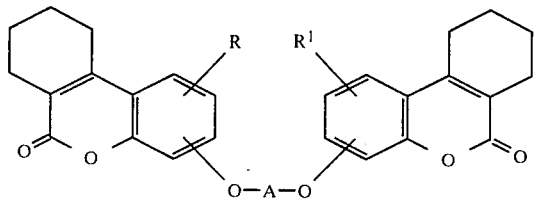

where R and R[1] independently represent hydrogen or methyl; where A is

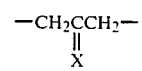

and where X represents single substitution with oxygen or substitution with hydrogen and a second group taken to be hydrogen, hydroxyl, amino, $C_1$-$C_4$ alkylamino or an acyloxy radical

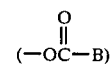

where B represents $C_1$-$C_{15}$ alkyl, $-CH_2CH_2COOH$, or (dimethylamino)phenyl. Also included are pharmaceutically acceptable salt forms of the compounds.

These compounds are useful as sedatives and/or for the protection of warm blooded animals from the effects of oxygen deprivation.

19 Claims, No Drawings

BIS-(DIBENZO[B,D]PYRANYLOXY) PROPANES

BACKGROUND OF THE INVENTION

This invention relates generally to dibenzopyrone derivatives and more specifically to certain 1,3-bis(7,8,9,10-tetrahydro-6-oxo-6H-dibenzo[b,d-]pyranyloxy) propanes and pharamaceutically acceptable salt forms which possess useful depressant and/or antihypoxia activity.

The compounds of the invention are structurally related to the compounds of applicant's pending application Ser. No. 749,321 filed June 27, 1985 which also possess antihypoxia activity.

BRIEF SUMMARY OF THE INVENTION

In accordance with this invention there are provided 1,3-bis(dibenzo[b,d]pyranyloxy)propanes having the following structural formula 1:

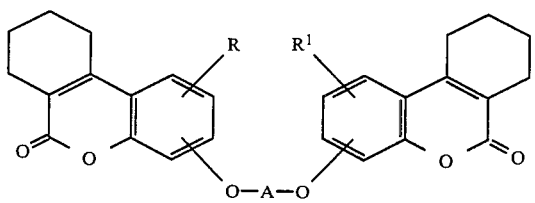

where R and $R^1$ independently represent hydrogen or methyl; where A is $$-CH_2\underset{X}{\overset{\|}{C}}CH_2-$$

and where X represents single substitution with oxygen or double substitution with hydrogen and a second group taken to be hydrogen, hydroxyl, amino, $C_1-C_4$ alkylamino or an acyloxy radical $$(-O\overset{O}{\overset{\|}{C}}-B)$$

where B represents $C_1-C_{15}$ alkyl, $-CH_2CH_2COOH$, or (dimethylamino)phenyl. Also included are pharmaceutically acceptable salt forms of the compounds.

These compounds possess useful depressant or antihypoxia activity, and are useful as sedatives and/or for the protection of warm blooded animals from the effects of oxygen deprivation.

DETAILED DESCRIPTION

The 1,3-bis(dibenzopyranyloxy)-2-propanols of formula 1, and R and $R^1$ represent hydrogen or methyl and X represents a substitution with hydrogen and hydroxyl, may be conveniently prepared from the readily synthesized 7,8,9,10-tetrahydro-6-oxo-6H-dibenzo[b,d]-pyrans of formula 2 (see R. Adams and B. R. Baker, *J. Am. Chem. Soc.*, 1940, 62, 2405) and 3 (see Preparation of Intermediates) where R represents hydrogen or methyl, by either of the two related methods (A or B) described below.

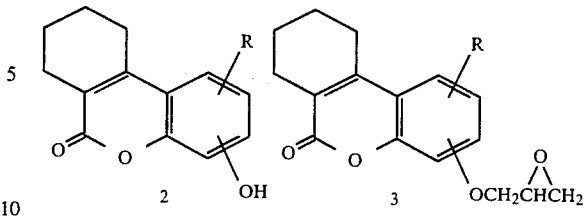

Method A consists of reacting a phenolic dibenzo[b,d]pyran derivative of formula 2 with a strong base, preferably an alkali metal hydroxide such as sodium hydroxide in a highly polar inert solvent system such as a dimethylsulfoxide/water mixture, to generate the corresponding phenolic anion. This anion is then reacted with a linear three carbon atom fragment containing groups activated for nucleophilic displacement on the first and third carbons and containing a hydroxyl group or latent hydroxyl group on the second carbon. Preferably this three carbon unit is epichlorohydrin, and further it is important for maximum conversions to the compounds of formula 1, that these materials be reacted in about a 1 to 1 molar ratio. Higher excesses of epichlorohydrin result in increased conversion of compounds of formula 2 to compounds of formula 3 and various contaminating byproducts and markedly reduced conversion to the desired compounds of formula 1. Reaction as described above, combined with reaction temperatures of 20°-65° C. is generally sufficient to obtain excellent conversions to the compounds of formula 1, where R is hydrogen or methyl, and X represents substitution of hydrogen and hydroxyl. This method (A) represents the simplest method for the generation of these compounds of formula 1, however it has the limitation of only being able to generate symmetrically disubstituted 1,3-bis(dibenzo[b,d]pyranyloxy)-2-propanols (i.e. where the two groups attached to A are identical).

As a specific example of this method, reaction of 7,8,9,10-tetrahydro-3-hydroxy-6-oxo-6H-dibenzo[b,d]-pyran with sodium hydroxide in 1:1 by volume dimethylsulfoxide:water for 15 min., and subsequent treatment with one mole equivalent of epichlorohydrin and heating to 40° C. for 72 hours gave a 65% isolated yield of 1,3-bis(7,8,9,10-tetrahydro-6-oxo-6H-dibenzo[b,d-]pyranyl-3-oxy)-2-propanol.

As mentioned above, Method A provides an extremely useful and simple method for obtaining the symmetrical compounds of formula 1. A second method is provided (,Method B) which is capable of generating both the symmetric and unsymmetric 1,3-bis(dibenzo[b,d]pyranyloxy)-2-propanols of formula 1. Method B consists of reacting the same anions generated from compounds of formula 2 in a highly polar inert solvent, such as a dimethylsulfoxide-water mixture, with a preformed epoxide of formula 3, as described above, to give a 1,3-bis(dibenzopyranyloxy)-2-propanol of formula 1 in which the dibenzopyranyloxy fragment is either the same or different depending on the choice of compound of formula 2 and formula 3. As a specific example of this method, treatment of one mole equivalent of 7,8,9,10-tetrahydro-3-hydroxy-6-oxo-6H-dibenzo[b,d]pyran with one mole equivalent of sodium hydroxide in 1:1 by volume dimethylsulfoxide:water, followed by the addition of one mole equivalent of 7,8,9,10-tetrahydro-3-methyl-1-(oxiranyl-methoxy)-6- oxo-6H-dibenzo[b,d]pyran at 60° C. gives a 65% yield of 1-(7,8,9,10-tetrahydro-6-oxo-6H-dibenzo[b,d]pyranyl-3-oxy)-3-(7,8,9,10-tetrahydro[b,d]pyranyl-1-oxy)-2-propanol.

The 1,3-bis(dibenzopyranyloxy)-2-propanols of formula 1, prepared by Methods A and B described above not only have useful activity in their own right, but also serve as intermediates for the preparation of the other compounds of formula 1, disclosed in the present invention.

Oxidation of these compounds of formula 1, where R and R' are hydrogen or methyl, and X represents a substitution with hydrogen and hydroxyl, with an oxidizing agent such as acetic anhydride in dimethylsulfoxide (Moffat oxidation) produces the corresponding compound of formula 1, where X is singly substituted with oxygen. For example, treatment of a solution of 1,3-bis(7,8,9,10-tetrahydro-6-oxo-6H-dibenzo[b,d]pyranyl-3-oxy)-2-propanol in dimethylsulfoxide at 50° C. with a 8–10 mole excess of acetic anhydride, and heating to 90° C. for 2 hours, gives an 88% yield of 1,3-bis(7,8,9,10-tetrahydro-6-oxo-6H-dibenzo[b,d]pyranyl-3-oxy)-2-propanone.

These ketones of formula 1, where X is oxygen, can be converted to the amines of formula 1, that is, the compounds of formula 1 where X represents a substitution with hydrogen and a second group taken to be amino or ($C_1$-$C_4$) alkylamino, by several known procedures preferably by reductive amination using an appropriate amine salt and a reducing agent, preferably sodium cyanoborohydride. For example, reaction of 1,3-bis(7,8,9,10-tetrahydro-6-oxo-6H-dibenzo[b,d]pyranyl-3-oxy)-2-propanone with methylamine hydrochloride and sodium cyanoborohydride in a mixture of chloroform and methanol gives the corresponding N-methyl-N-[1,3-bis(7,8,9,10-tetrahydro-6-oxo-6H-dibenzo[b,d]pyranyl-3-oxy)-2-propyl]amine. Ammonia salts and a wide variety of amine salts may be reacted in this manner to produce the corresponding amino compounds of formula 1. Salts of methylamine, ethylamine, isopropylamine, n-propylamine, n-butylamine, t-butylamine and the like may be used as described above.

Additionally, the compounds of formula 1, where X is substituted with hydrogen and hydroxyl generated by Methods A or B, may be used to prepare various ester derivatives of formula 1, where X is substituted with hydrogen and an acyloxy radical

where B represents $C_1$-$C_{15}$ alkyl, —$CH_2CH_2COOH$ or (dimethylamino)phenyl, by utilizing normal ester forming reactions, such as, reaction with appropriate acid chloride in the presence of an acid acceptor like triethylamine or alternatively by reaction with sodium hydride and the appropriate acid anhydride. For example, reaction of 1,3-bis(7,8,9,10-tetrahydro-6-oxo-6H-dibenzo[b,d]pyranyl-3-oxy)-2-propanol with palmitoyl chloride ($CH_3(CH_2)_{14}COCl$) in chloroform in the presence of triethylamine gives the corresponding palmitate ester, 1,3-bis(7,8,9,10-tetrahydro-6-oxo-6H-dibenzo[b,d]pyranyl-3-oxy)-2-propyl palmitate; and reaction with sodium hydride and succinic anhydride in tetrahydrofuran gives the corresponding succinate ester, 1,3-bis(7,8,9,10-tetrahydro-6-oxo-6H-dibenzo[b,d]pyranyl-3-oxy)-2-propyl hydrogen succinate. A wide variety of ester derivatives of formula 1 may be readily synthesized as described above.

Some of the compounds of formula 1 do not contain acidic or basic functional groups and therefore no salt forms can be prepared for these compounds and they must be used as is. However, some of the compounds of general formula 1, do contain acidic or basic groups and various pharmaceutically acceptable salt forms may be prepared. Acid addition salts may be prepared from the compounds of formula 1 containing basic groups by treatment with mineral or organic acids such as hydrochloric, hydrobromic, sulfuric, phosphoric, acetic, lactic, maleic, fumaric, succinic, citric, tartaric, methanesulfonic, or toluenesulfonic acids or the like. Base addition salts are prepared from the compounds of formula 1 containing acidic groups by treatment with inorganic or organic bases such as lithium, sodium, potassium, calcium, barium, aluminum and magnesium hydroxides or ammonia, methylamine, aminoethanol, dimethylaminoethanol, nicotine, ethylenediamine, cyclohexylamine and the like.

The antihypoxia activity of the compounds of this invention was determined by a study of their ability to protect mice from death due to the lack of oxygen in an environmental chamber flushed with a 96% nitrogen/4% oxygen atmosphere, a condition resulting in normobaric hypoxia. The time to death of groups of five or more treated mice were statistically compared with matched groups of untreated mice and the minimum active dose (MAD) and/or the dose which produced a 100% increase in survival time (100%S) was determined. The compounds of formula 1 demonstrated activity in these studies at MAD's usually ranging from 0.1–400 mg/kg and at 100%S's usually ranging from 4–400 mg/kg after intraperitoneal dosing. The compounds of this invention were also notable in their lack of toxic effects.

The following specific nonlimiting procedures and examples are provided to illustrate the preparation of the various compounds of formula 1.

PREPARATION OF INTERMEDIATES

Procedure 1

Preparation of 7,8,9,10-tetrahydro-3-methyl-1-(oxiranylmethoxy)-6-oxo-6H-dibenzo[b,d]pyran To a stirred solution of NaOH (4.0 g, 0.1 m) in dimethylsulfoxide (DMSO) (250 ml) and water (250 ml), was added 7,8,9,10-tetrahydro-1-hydroxy-3-methyl-6-oxo-6H-dibenzo[b,d]pyran (20.0 g, 0.87 m) and the mixture stirred for 5 minutes, then treated with epichlorohydrin (50 ml). After 5 hours the mixture was cooled in an ice bath for 30 minutes and the precipitated solid collection by filtration, washed with water and dried to give 7,8,9,10-tetrahydro-3-methyl-1-(oxiranylmethoxy)-6-oxo-6H-dibenzo[b,d]pyran as a white solid, mp. 164°–165° C. An analytical sample recrystallized from methanol melted at 165°–166° C.

Procedure 2

Preparation of 7,8,9,10-tetrahydro-3-(oxiranylmethoxy)-6-oxo-6H-dibenzo[b,d]pyran To a stirred solution of NaOH (2.0 g, 0.05 m) in DMSO (125 ml) and water (125 ml) was added 7,8,9,10-tetrahydro-3-hydroxy-6-oxo-6H-dibenzo[b,d]pyran (10.0 g, 0.046 m). When a solution was obtained, the mixture was treated with epichlorohydrin (35 ml) and stirred for 56 hours. A white solid precipitated which was collected by filtration to give 12.1 g of a mixture consisting of ca. 90% 7,8,9,10-tetrahydro-3-(oxiranylmethoxy)-6-oxo-6H-dibenzo[b,d]pyran. The pure epoxide was obtained by chromatography on SiO$_2$ and crystallization from methanol/chloroform to give 8.0 g of white solid, mp. 120°–121° C.

EXAMPLES

Example 1

Preparation of 1,3-bis(7,8,9,10-tetrahydro-6-oxo-6H-dibenzo[b,d]pyranyl-3-oxy)-2-propanol (Method A)

To a stirred solution of sodium hydroxide (2.0 g, 0.05 mol) in 250 ml of 1:1 by volume DMSO:H$_2$O was added 7,8,9,10-tetrahydro-3-hydroxy-6-oxo-6H-dibenzo[b,d]pyran (10.0 g, 0.0463 mol) and then epichlorohydrin (4.625 g, 0.05 mol) and the mixture stirred at 25° C. for 24 hrs. The white solid which had crystallized was collected by filtration, air dried, and recrystallized from 95% ethanol to give, after vacuum drying, 6.8 g of 1,3-bis(7,8,9,10-tetrahydro-6-oxo-6H-dibenzo[b,d]pyranyl-3-oxy)-2-propanol, mp. 188°–190° C.

Example 2

Preparation of 1-(7,8,9,10-tetrahydro-6-oxo-6H-dibenzo[b,d]pyranyl-3-oxy)-3-(7,8,9,10-tetrahydro-3-methyl-6-oxo-6H-dibenzo[b,d]pyranyl-1-oxy)-2-propanol (Method B)

To a stirred solution of sodium hydroxide (0.8 g, 0.02 mol) in 500 ml 1:1 by volume DMSO:H$_2$O was added 7,8,9,10-tetrahydro-3-hydroxy-6-oxo-6H-dibenzo[b,d]pyran (4.32 g, 0.02 mol) and the mixture heated to 60° C. and then treated with a solution of 7,8,9,10-tetrahydro-3-methyl-1-(oxiranylmethoxy)-6-oxo-6H-dibenzo[b,d]pyran (5.8 g, 0.02 mol) in 400 ml hot DMSO (60° C.) and the mixture stirred for 6 hrs., cooled and treated with 500 ml water. The solid which had crystallized was collected by filtration (6.8 g) and dissolved in refluxing methanol (100 ml) and chloroform (75 ml), hot filtered, and allowed to recrystallize. The white solid was collected by filtration to give 1-(7,8,9,10-tetrahydro-6-oxo-6H-dibenzo[b,d]pyranyl-3-oxy)-3-(7,8,9,10-tetrahydro-3-methyl-6-oxo-6H-dibenzo[b,d]pyranyl-1-oxy)-2-propanol, mp. 230°–231° C.

Example 3

Preparation of 1,3-bis(7,8,9,10-tetrahydro-3-methyl-6-oxo-6H-dibenzo[b,d]pyranyl-1-oxy)-2-propanol (Method B)

To a stirred solution of sodium hydroxide (0.8 g, 0.02 mol) in 500 ml of 1:1 by volume DMSO:H$_2$O was added 7,8,9,10-tetrahydro-1-hydroxy-3-methyl-6-oxo-6H-dibenzo[b,d]pyran (4.64 g, 0.02 mol) and the mixture heated to 60° C. and treated with a solution of 7,8,9,10-tetrahydro-3-methyl-1-(oxiranylmethoxy)-6-oxo-6H-dibenzo[b,d]pyran (5.8 g, 0.02 mol) in 400 ml of hot (60° C.) DMSO. The mixture was stirred at 60° C. for 6 hrs., cooled, and treated with 500 ml water. The solid which had crystallized was collected by filtration and recrystallized twice from a mixture of methanol (100 ml) and chloroform (50 ml) to give 4.0 g of 1,3-bis(7,8,9,10-tetrahydro-3-methyl-6-oxo-6H-dibenzo[b,d]pyranyl-1-oxy)-2-propanol, mp. 224°–226° C.

Example 4

Preparation of 1,3-bis(7,8,9,10-tetrahydro-6-oxo-6H-dibenzo[b,d]pyranyl-3-oxy)-2-propanone A stirred solution of 1,3-bis(7,8,9,10-tetrahydro-6-oxo-6H-dibenzo[b,d]pyranyl-3-oxy)-2-propanol (10.88 g, 0.04 mol) in dimethylsulfoxide (500 ml) at 50° C. was treated with acetic anhydride (38.4 ml, 0.256 mol) and the mixture heated to 90° C. for 2 hrs., then allowed to cool slowly to ambient temperature (16 hrs.). The solid which crystallized was collected by filtration, washed with DMSO (2×150 ml), washed with methanol (3×100 ml) and dried to give 9.5 g of 1,3-bis(7,8,9,10-tetrahydro-6-oxo-6H-dibenzo[b,d]pyranyl-3-oxy)-2-propanone, mp. 246°–247° C.

Using the procedure described hereinabove and substituting 1,3-bis(7,8,9,10-tetrahydro-3-methyl-6-oxo-6H-dibenzo[b,d]pyranyl-1-oxy)-2-propanol or 1-(7,8,9,10-tetrahydro-6-oxo-6H-dibenzo[b,d]pyranyl-3-oxy)-3-(7,8,9,10-tetrahydro-3-methyl-6-oxo-6H-dibenzo[b,d]pyranyl-1-oxy)-2-propanol for 1,3-bis(7,8,9,10-tetrahydro-6-oxo-6H-dibenzo[b,d]pyranyl-3-oxy)-2-propanol will provide the corresponding ketones 1,3-bis(7,8,9,10-tetrahydro-3-methyl-6-oxo-6H-dibenzo[b,d]pyranyl-1-oxy)-2-propanone or 1-(7,8,9,10-tetrahydro-6-oxo-6H-dibenzo[b,d]pyranyl-3-oxy)-3-(7,8,9,10-tetrahydro-3-methyl-6-oxo-6H-dibenzo[b,d]pyranyl-1-oxy)-2-propanone, respectively.

Example 5

Preparation of 1,3-bis(7,8,9,10-tetrahydro-6-oxo-6H-dibenzo[b,d]pyranyl-3-oxy)-2-propylamine hydrochloride A stirred solution of 1,3-bis(7,8,9,10-tetrahydro-6-oxo-6H-dibenzo[b,d]pyranyl-3-oxy)-2-propanone (3.7 g, 0.0137 mol) in refluxing chloroform (4 L) was treated with a solution of ammonium acetate (10.54 g, 0.137 mol) in 100 ml methanol, and the mixture allowed to cool to 35° C., then treated with a solution of NaCNBH$_4$ (0.86 g, 0.0137 mol) in methanol (50 ml), and stirred at ambient temperature for 24 hrs. Water (1 L) and 10 ml of 50% by weight NaOH were added, the mixture stirred for 30 min., and additional 1 L of water added and the layers were separated. The chloroform layer was washed with water (1.5 L) and dried over MgSO$_4$. Evaporation of the solvent gave 4.5 g of the crude product, which was purified by chromatography on SiO$_2$ eluting with 1% by volume CH$_3$OH/CHCl$_3$. The hydrochloride salt was formed by treating a solution of the pure product from above in a mixture of methanol (125 ml) and chloroform (75 ml) with HCl gas. The white solid so obtained was twice suspended in 100 ml of refluxing methanol, recovered by filtration, then vacuum dried to give 1,3-bis(7,8,9,10-tetrahydro-6-oxo-6H-dibenzo[b,d]pyranyl-3-oxy)-2-propylamine hydrochloride, mp. 293°–294° C.

Example 6

Preparation of
N-methyl-N-[1,3-bis(7,8,9,10-tetrahydro-6-oxo-6H-dibenzo[b,d]pyranyl-3-oxy)-2-propyl]amine hydrochloride A stirred solution of 1,3-bis(7,8,9,10-tetrahydro-6-oxo-6H-dibenzo[b,d]pyranyl-3-oxy)-2-propanone (5.0 g, 0.0185 mol) in 4 L of refluxing chloroform was treated with a solution of methylamine hydrochloride (12.48 g, 0.185 mol) in 100 ml of methanol, and the mixture cooled to 35° C. then treated with a solution of NaCNBH$_4$ (1.16 g, 0.0185 mol) in 50 ml of methanol and stirred at ambient temperature for 24 hrs. Sodium hydroxide (0.5% by weight, 1 L) was added, the mixture stirred for 1 hr., water (1 L) added and the layers separated. The chloroform layer was washed with water (2 L), dried over MgSO$_4$ and evaporated to a foamy solid, 5.4 g, which was combined with a second identical lot of material and purified by chromatography on SiO$_2$ eluting with 1% by volume CH$_3$OH in CHCl$_3$ to afford 3.4 g of the pure product as a yellow oil. The hydrochloride salt was prepared by treating a solution of the above amine in 75 ml methanol and 10 ml chloroform with HCl gas. A white solid crystallized which was collected by filtration and vacuum dried to give 2.85 g of N-methyl-N-[1,3-bis(7,8,9,10-tetrahydro-6-oxo-6H-dibenzo[b,d]pyranyl-3-oxy)-2-propyl]amine hydrochloride, mp. 274°–275° C.

Using the procedure described above and substituting ethylamine, n-propylamine, i-propylamine, n-butylamine or t-butylamine hydrochloride for methylamine hydrochloride and using the appropriate ketone from Example 4, will provide the corresponding amine of formula 1, where R represents hydrogen or methyl, and X represents substitution with hydrogen and (C$_1$–C$_4$) alkylamine.

Example 7

Preparation of
1,3-bis(7,8,9,10-tetrahydro-6-oxo-6H-dibenzo[b,d]pyranyl-3-oxy)-2-propyl hydrogen succinate To a stirred suspension of 1,3-bis(7,8,9,10-tetrahydro-6-oxo-6H-dibenzo[b,d]pyranyl-3-oxy)-2-propanol (10.0 g, 0.02 mol) in 500 ml of tetrahydrofuran under nitrogen was added 50% by weight NaOH (0.57 g, 0.024 mol) and the mixture heated to reflux for 1 hr., treated with succinic anhydride (2.2 g, 0.022 mol) and refluxed for 96 hrs. The cooled reaction mixture was poured into 1 L of saturated ammonium chloride and the layers separated. The aqueous phase was extracted with chloroform (3×750 ml) and the combined organic phases dried over MgSO$_4$ and evaporated to a solid residue, 11.0 g. This material was purified by chromatography on SiO$_2$ eluting with 3% by volume methanol/chloroform and dried at 90° C. for 48 hrs. to give 2.9 g of 1,3-bis(7,8,9,10-tetrahydro-6-oxo-6H-dibenzo[b,d]pyranyl-3-oxy)-2-propyl hydrogen succinate, mp. 199°–200° C.

Using the general procedure disclosed above and substituting other propanols of formula 1, where R and R$^1$ are hydrogen or methyl and X represents substitution with hydrogen and hydroxyl for 1,3 bis(7,8,9,10-tetrahydro-6-6H-dibenzo[b,d]pyranyl-3-oxy)-2-propanol in the above example will provide the corresponding succinate esters of formula 1, where R and R$^1$ are hydrogen or methyl and where X represents substitution with hydrogen and an acyloxy radical

where B is —CH$_2$CH$_2$COOH.

Example 8

Preparation of
1,3-bis(7,8,9,10-tetrahydro-6-oxo-6H-dibenzo[b,d]pyranyl-3-oxy)-2-propyl acetate To a solution of 1,3-bis(7,8,9,10-tetrahydro-6-oxo-6H-dibenzo[b,d]pyranyl-3-oxy)-2-propanol (5.0 g, 0.0107 mol) in 500 ml chloroform under nitrogen was added triethylamine (12.4, 0.12 mol) and acetyl chloride (0.87 g, 0.012 mol) and the mixture refluxed for 18 hrs., cooled, then washed with (3×100 ml) of dilute hydrochloric acid, (3×100 ml) water and dried over MgSO$_4$. The solvent was evaporated to a solid residue (5.1 g) which was slurried in 400 ml of hot ethanol, collected by filtration and vacuum dried to give 4.01 g of 1,3-bis(7,8,9,10-tetrahydro-6-oxo-6H-dibenzo[b,d]pyranyl-3-oxy)-2-propyl acetate mp. 201°–202° C.

Example 9

Preparation of
1,3-bis(7,8,9,10-tetrahydro-6-oxo-6H-dibenzo[b,d]pyranyl-3-oxy)-2-propyl palmitate To a stirred solution of 1,3-bis(7,8,9,10-tetrahydro-6-oxo-6H-dibenzo[b,d]pyranyl-3-oxy)-2-propanol (10.0 g, 0.02 mol) in 500 ml of chloroform under nitrogen was added triethylamine (12.4 g, 0.12 mol) and palmitoyl chloride (10.9 g, 0.04 mol) and the mixture refluxed for 96 hrs., cooled, then washed with 3×200 ml) dilute hydrochloric acid, (3×200 ml) water, and dried over MgSO$_4$. The solvent was evaporated to an oil which was purified by chromatography on SiO$_2$ eluting with 3% by volume CH$_3$OH/CHCL$_3$. The purified product was recrystallized twice from 200 ml of ethanol to give 11.6 g of 1,3-bis(7,8,9,10-tetrahydro-6-oxo-6H-dibenzo[b,d]pyranyl-3-oxy)-2-propyl palmitate, mp. 90°–91° C.

Using the procedure outlined above and in Example 8 and substituting an acid chloride of formula

where B is (C$_2$–C$_{14}$) alkyl, for acetyl chloride (B=C$_1$ alkyl) in Example 8 or palmitoyl chloride (B=C$_{15}$ alkyl) in Example 9 will provide the corresponding compounds of formula 1, where X represents substitution with hydrogen and an acyloxy radical,

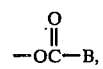

where B is (C$_2$–C$_{14}$) alkyl.

Example 10

Preparation of
1,3bis(7,8,9,10-tetrahydro-6-oxo-6H-dibenzo[b,d]pyranyl-3-oxy)-2-propyl 4-(dimethylamino)benzoate To a stirred solution of 1,3-bis(7,8,9,10-tetrahydro-6-oxo-6H-dibenzo[b,d]pyranyl-3-oxy)-2-propanol (10.0 g, 0.02 mol) in 500 ml of chloroform under nitrogen was added triethylamine (30.0 g, 0.29 mol) and 4-(dimethylamino) benzoyl chloride. HCl (27.2 g, 0.14 mol) and the mixture stirred for 48 hrs., then poured into 1 L of 5% by volume HCl. The organic layer was washed with 5% HCl (2×750 ml), water 2×750 ml), and dried over MgSO$_4$. Evaporation of the solvent gave an oily residue which was purified by chromatography on SiO$_2$ eluting with chloroform, and crystallized from chloroform (25 ml) and ethylacetate (200 ml) to give 4.5 g of 1,3-bis(7,8,9,10-tetrahydro-6-oxo-6H-dibenzo[b,d]pyranyl-3-oxy)-2-propyl 4-(dimethylamino) benzoate, mp. 217°–218° C.

I claim:

1. A compound having the formula:

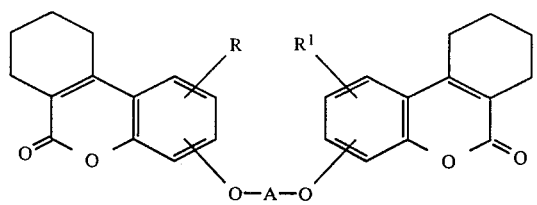

where R and R$^1$ independently represent hydrogen or methyl; where A is;

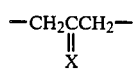

and where X represents single substitution with oxygen or substitution with hydrogen and a second group taken to be hydrogen, hydroxyl, amino, C$_1$–C$_4$ alkylamino or an acyloxy radical

where B represents C$_1$–C$_{15}$ alkyl, —CH$_2$CH$_2$COOH, or (dimethylamino)phenyl.

2. A compound according to claim 1 which contains an acid group.

3. A base addition salt of the compound according to claim 2.

4. A compound according to claim 1 which contains a basic group.

5. An acid addition salt of the compound of claim 4.

6. A compound according to claim 1 wherein X represents oxygen.

7. A compound according to claim 1 wherein X represents hydrogen and hydroxyl.

8. A compound according to claim 1 wherein the compound is symmetrical.

9. A compound according to claim 1 wherein the compound is unsymmetrical.

10. A compound according to claim 1 where the compound is 1,3-bis(7,8,9,10-tetrahydro-6-oxo-6H-dibenzo[b,d]pyranyl-3-oxy)-2-propanol.

11. A compound according to claim 1 where the compound is 1-(7,8,9,10-tetrahydro-6-oxo-6H-dibenzo[b,d]pyranyl-3-oxy)-3-(7,8,9,10-tetrahydro-3-methyl-6-oxo-6H-dibenzo[b,d]pyranyl-1-oxy)-2-propanol.

12. A compound according to claim 1 where the compound is 1,3-bis(7,8,9,10-tetrahydro-3-methyl-6-oxo-6H-dibenzo[b,d]pyranyl-1-oxy)-2-propanol.

13. A compound according to claim 1 where the compound is 1,3-bis(7,8,9,10-tetrahydro-6-oxo-6H-dibenzo[b,d]pyranyl-3-oxy)-2-propanone.

14. A compound according to claim 5 where the compound is 1,3-bis(7,8,9,10-tetrahydro-6-oxo-6H-dibenzo[b,d]pyranyl-3-oxy)-2-propylamine hydrochloride.

15. A compound according to claim 5 where the compound is N-methyl-N-[1,3-bis(7,8,9,10-tetrahydro-6-oxo-6H-dibenzo[b,d]pyranyl-3-oxy)-2-propyl]amine hydrochloride.

16. A compound according to claim 1 where the compound is 1,3-bis(7,8,9,10-tetrahydro-6-oxo-6H-dibenzo[b,d]pyranyl-3-oxy)-2-propyl hydrogen succinate.

17. A compound according to claim 1 where the compound is 1,3-bis(7,8,9,10-tetrahydro-6-oxo-6H-dibenzo[b,d]pyranyl-3-oxy)-2-propyl acetate.

18. A compound according to claim 1 where the compound is 1,3-bis(7,8,9,10-tetrahydro-6-oxo-6H-dibenzo[b,d]pyranyl-3-oxy)-2-propyl palmitate.

19. A compound according to claim 1 where the compound is 1,3-bis(7,8,9,10-tetrahydro-6-oxo-6H-dibenzo[b,d]pyranyl-3-oxy)-2-propyl 4-(dimethylamino)benzoate.

* * * * *